United States Patent [19]
Jeschke et al.

[11] Patent Number: 6,033,879
[45] Date of Patent: Mar. 7, 2000

[54] PROCESS FOR THE PREPARATION OF SUBSTITUTED ARYL LACTIC ACID CONTAINING CYCLODEPSIPEPTIDES WITH 24 RING ATOMS

[75] Inventors: Peter Jeschke, Leverkusen; Gerhard Bonse, Köln; Gerhard Thielking, Burscheid; Winfried Etzel, Leichlingen; Achim Harder, Köln; Norbert Mencke, Leverkusen; Horst Kleinkauf; Rainer Zocher, both of Berlin, all of Germany; Katsuharu Iinuma, Yokohama, Japan; Kouichi Miyamoto, Berlin, Germany

[73] Assignee: Bayer Aktiengesellschaft, Leverkusen, Germany

[21] Appl. No.: 09/077,913

[22] PCT Filed: Nov. 25, 1996

[86] PCT No.: PCT/EP96/05190

§ 371 Date: Jun. 4, 1998

§ 102(e) Date: Jun. 4, 1998

[87] PCT Pub. No.: WO97/20945

PCT Pub. Date: Jun. 12, 1997

[30] Foreign Application Priority Data

Dec. 7, 1995 [DE] Germany .................. 195 45 639

[51] Int. Cl.[7] .................. C12P 21/04; C12P 1/02
[52] U.S. Cl. .................. 435/71.1; 514/11; 530/317; 530/321; 435/171; 435/254.1; 435/911
[58] Field of Search .................. 435/71.1, 254.1, 435/911, 171; 514/11; 530/317, 321

[56] References Cited

U.S. PATENT DOCUMENTS

| | | | |
|---|---|---|---|
| 4,879,223 | 11/1989 | Miyazawa et al. | 435/60 |
| 5,116,815 | 5/1992 | Takagi et al. | 514/11 |
| 5,747,448 | 5/1998 | Ohyama et al. | 514/11 |
| 5,763,221 | 6/1998 | Aoyagi et al. | 435/69.1 |

FOREIGN PATENT DOCUMENTS

| | | |
|---|---|---|
| 288087 | 10/1988 | European Pat. Off. . |
| 382173 | 8/1990 | European Pat. Off. . |
| 780468 | 6/1997 | European Pat. Off. . |
| 98/05655 | 2/1998 | WIPO . |

OTHER PUBLICATIONS

Database WPI, Section Ch, Week 9431, Derwent Publications Ltd., AN 94–252800 XP002026183 & JP 06 184 126 A Jul. 5, 1994.

Chemical Abstracts, vol. 117, No. 7, Aug. 17, 1992, Abstract No. 62356, Sasaki, Toru, et al. "A new anthelmintic . . . PF1022A" XP002026182 see abstract and J. Antibiot. (1992), 45(5), 692–7 CODEN: JANTAJ;ISSN: 0021–8820.

Biosci., Biotechnol., Biochem. (1993), 57(1), 98–101 CODEN: BBBIEJ, XP002026181 Kawazu, Kazuyoshi, et al. "Isolation and . . . D1084".

Primary Examiner—Herbert J. Lilling
Attorney, Agent, or Firm—Joseph C. Gil; Godfried R. Akorli

[57] ABSTRACT

The present invention relates to a new process for the preparation of substituted aryllactic acid-containing cyclodepsipeptides having 24 ring atoms of the formula (I):

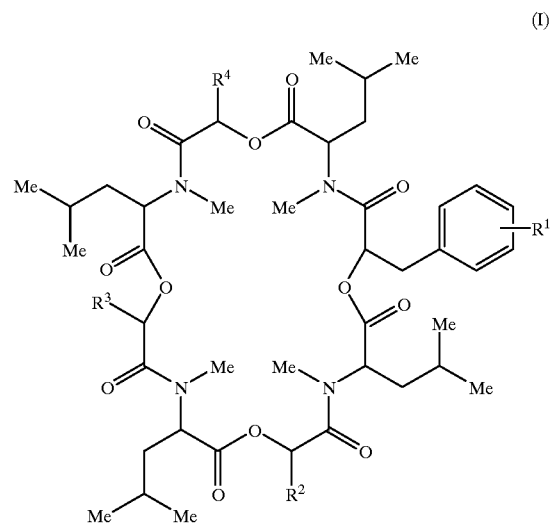

(I)

in which $R^1$, $R^2$, $R^3$, $R^4$ have the meaning given in the description, with the aid of fungal strains of the species Agonomycetales or enzymatic preparations isolated therefrom.

1 Claim, No Drawings

PROCESS FOR THE PREPARATION OF SUBSTITUTED ARYL LACTIC ACID CONTAINING CYCLODEPSIPEPTIDES WITH 24 RING ATOMS

The present invention relates to a new process for the preparation of substituted aryllactic acid-containing cyclodepsipeptides having 24 ring atoms, some of which are known.

The preparation of various cyclic, aryllactic acid-containing depsipeptides having 24 ring atoms by microbial processes, for example PF 1022A, PF 1022 B, PF 1022 C, PF 1022D and PF 1022E, has already been described (cf. fermentation of cyclooctadepsipeptides: PF 1022A from Mycelia sterilia (FERM BP-2671; former designation FERM P-10 504) in EP-OS (European Published Specification) 382 173; T. Sasaki et al., J. Antibiotics 45, 1992, pp. 692–697; from the same culture were isolated: PF 1022B, PF 1022C and PF 1022D; JP-Pat. 5 170 749; PF 1022E: JP-Pat. 6 184 126).

The compounds of the PF 1022 series have the following formula (I):

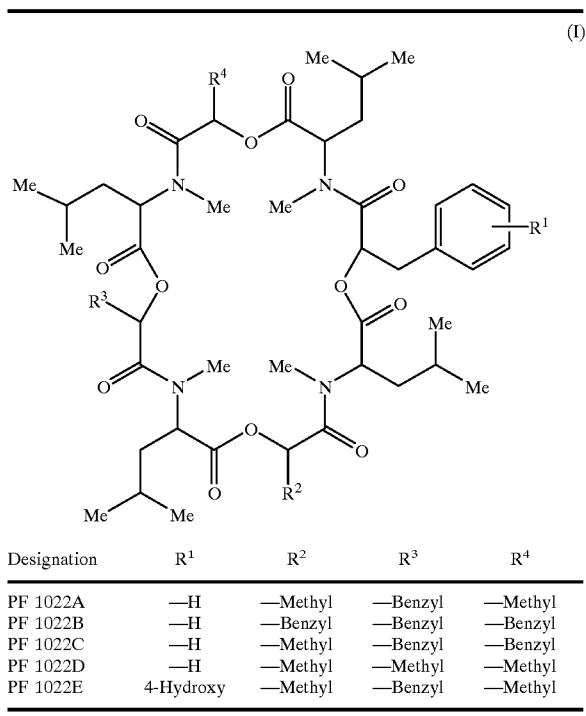

| Designation | $R^1$ | $R^2$ | $R^3$ | $R^4$ |
|---|---|---|---|---|
| PF 1022A | —H | —Methyl | —Benzyl | —Methyl |
| PF 1022B | —H | —Benzyl | —Benzyl | —Benzyl |
| PF 1022C | —H | —Methyl | —Benzyl | —Benzyl |
| PF 1022D | —H | —Methyl | —Methyl | —Methyl |
| PF 1022E | 4-Hydroxy | —Methyl | —Benzyl | —Methyl |

It has also already been disclosed that a number of cyclic, aryllactic acid-containing depsipeptides having 24 ring atoms can be prepared by means of chemical synthetic processes (cf. total syntheses of cyclooctadepsipeptides: JP Pat. 5 229 997; JP Pat. 5 320 1 48; Makoto Ohyama et al., Biosci. Biotech. Biochem. 58 (6), 1994, pp. 1193–1194; Makio Kobayshi et al., Annu. Rep. Sankyo Res. Lab. 46, 1994, pp. 67–75; Stephen J. Nelson et al., J. Antibiotics 47, (11), 1994, pp. 1322–1327; J. Scherkenbeck et al. Tetrahedron 51 (31), 1995, pp. 8459–8470 [PF 1022A]; WO 94/19334; WO 95/19053; EP-OS [European Published Specification] 634 408; EP-OS [European Published Specification] 626 375; EP-OS [European Published Specification] 626 376).

It is furthermore known that certain aryllactic acid-containing cyclodepsipeptides having 24 ring atoms can be used as endoparasiticides (cf. e.g.: EP-OS [European Published Specification] 382; EP-OS [European Published Specification] 503 538; WO 93/19053; EP-OS [European Published Specification] 0 634 408; WO 94/19334; WO 95/07272; EP-OS [European Published Specification] 626 375; EP-OS [European Published Specification] 626 376).

While chemical synthetic processes make possible a wide variation of the substituent $R^1$ in the phenyllactic acid fragment of certain cyclooctadepsipeptides (cf.: WO 94/19334; WO 95/19053; EP-OS [European Published Specification] 634 408; EP-OS [European Published Specification] 626 375; EP-OS [European Published Specification] 626 376), until now in the microbial processes only the unsubstituted D-phenyllactic acid-containing cyclooctadepsipeptides preferably resulted ($R^1$=-H; cf.: PF 1022A, PF 1022B, PF 1022C and PF 1022D).

Apart from the already-mentioned fermentation of the D-(4-hydroxyphenyl)lactic acid-containing cyclooctadepsipeptide PF 1022E ($R^1$=4-hydroxy; cf.: JP Pat. 6 184 126), the fermentative preparation of other, substituted aryllactic acid-containing cyclooctadepsipeptides has thus not been disclosed until now.

The present invention therefore relates to a process for the preparation of substituted aryllactic acid-containing cyclodepsipeptides having 24 ring atoms with the aid of fungal strains of the species Agonomycetales or enzymatic preparations isolated therefrom.

In the process according to the invention, the substituted aryllactic acid-containing cyclodepsipeptides having 24 ring atoms of the general formula (I)

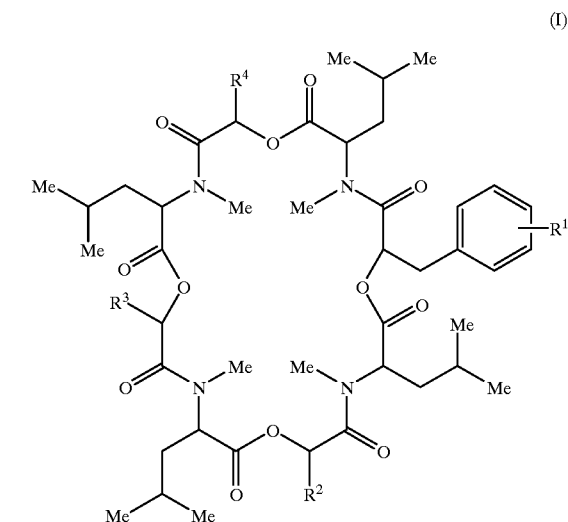

in which $R^1$ represents straight-chain or branched alkyl, cyclic alkyl, alkenyl, alkoxy, alkenyloxy, arylalkoxy, cycloalkoxy, alkylamino, dialkylamino, alkylcarbonyl, alkylcarbonyloxy, alkoxycarbonyl, alkylaminocarbonyl, dialkylaminocarbonyl, heteroarylcarbonyl, alkoxysulphonyl, alkylaminosulphonyl, dialkylaminosulphonyl, alkylthio, alkylsulphinyl, alkylsulphonyl, heteroarylsulphonyl, each of which can optionally be substituted, hydroxyl, halogen, nitro, amino, carboxyl, carbamoyl, cyano, or, if appropriate substituted cyclic amino groups, and $R^2$, $R^3$ and $R^4$ independently of one another represent represents straight-chain or branched alkyl, heteroarylmethyl or a benzyl radical which is optionally substituted by radicals from the series consisting of hydrogen, straight-chain or branched alkyl, cyclic alkyl, alkenyl, alkoxy, alkenyloxy, arylalkoxy, cycloalkoxy, alkylamino, dialkylamino, alkylcarbonyl, alkylcarbonyloxy, alkoxycarbonyl, alkylaminocarbonyl, dialkylaminocarbonyl, heteroarylcarbonyl, alkoxysulphonyl, alkylaminosulphonyl, dialkylaminosulphonyl, alkylthio, alkylsulphinyl, alkylsulphonyl, heteroarylsulphonyl, each of which can optionally be substituted, hydroxyl, halogen, nitro, amino, carboxyl, carbamoyl, cyano, or which is optionally substituted by a suitable cyclic amino group, with the exception of the compounds of the formula (I), in which $R^1$ represents 4-hydroxyl, $R^3$ represents unsubstituted benzyl and the other radicals have the abovementioned meaning, are prepared by reacting a) optically active or racemic amino acids of the general formulae (II), (III), (IV) and (V)

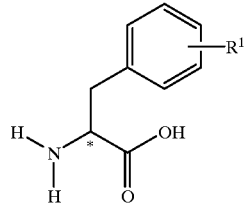
(II)

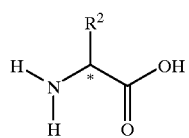
(III)

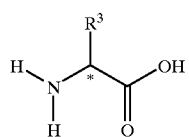
(IV)

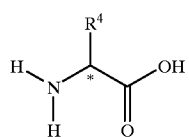
(V)

in which $R^1$, $R^2$, $R^3$ and $R^4$ have the meaning given above, or b) optically active or racemic 2-hydroxy-carboxylic acids of the general formulae (VI), (VII), (VIII) and (IX)

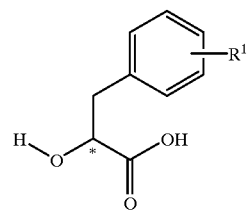
(VI)

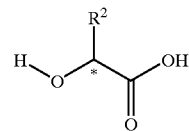
(VII)

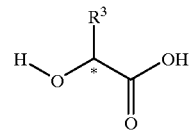
(VIII)

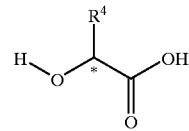
(IX)

in which $R^1$, $R^2$, $R^3$ and $R^4$ have the meaning given above, in the presence of fungal strains of the species Agonomycetales in suitable nutrient solutions or in the presence of synthetases isolated from these fungal strains in a buffer system and then isolating the desired, substituted aryllactic acid-containing cyclodepsipeptides having 24 ring atoms.

The aryllactic acid-containing cyclic depsipeptides having 24 ring atoms of the general formula (I) and their acid addition salts and metal salt complexes are outstandingly suitable for the control of endoparasites, particularly in the field of medicine and veterinary medicine.

Optionally substituted alkyl on its own or as a constituent of a radical in the general formulae denotes straight-chain or branched alkyl preferably having 1 to 6, in particular 1 to 4, carbon atoms. Examples which may be mentioned are optionally substituted methyl, ethyl, n-propyl, isopropyl, n-butyl, isobutyl, sec-butyl, tert-butyl, pentyl, 1-methylbutyl, 2-methylbutyl, 3-methylbutyl, 1,2-dimethylpropyl, 1,1-dimethylpropyl, 2,2-dimethylpropyl, 1-ethylpropyl, hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl and 2-ethylbutyl. Preferably, methyl, ethyl, n-propyl, isopropyl, n-butyl, isobutyl, sec-butyl and tert-butyl may be mentioned.

Optionally substituted alkenyl on its own or as a constituent of a radical in the general formulae denotes straight-chain or branched alkenyl preferably having 1 to 6, in particular 1 to 4, carbon atoms. Examples which may be mentioned are optionally substituted vinyl, 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2- propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl. Preferably, optionally substituted ethenyl, 2-propenyl, 2-butenyl or 1-methyl-2-propenyl may be mentioned.

Optionally substituted cycloalkyl on its own or as a constituent of a radical in the general formulae denotes mono-, bi- and tricyclic cycloalkyl, preferably having 3 to 10, in particular having 3, 5 or 7, carbon atoms. Examples which may be mentioned are optionally substituted cyclopropyl, cyclobutyl, cyclopentyl, cyclohexyl, cycloheptyl, cyclooctyl, bicyclo[2.2.1]heptyl, bicyclo[2.2.2]octyl and adamantyl.

Optionally substituted alkoxy on its own or as a constituent of a radical in the general formulae denotes straight-chain or branched alkoxy preferably having 1 to 6, in particular 1 to 4, carbon atoms. Examples which may be mentioned are optionally substituted methoxy, ethoxy, n-propoxy, isopropoxy, n-butoxy, isobutoxy, sec-butoxy and tert-butoxy.

Optionally substituted alkylthio on its own or as a constituent of a radical in the general formulae denotes straight-chain or branched alkylthio preferably having 1 to 6, in particular 1 to 4, carbon atoms. Examples which may be mentioned are optionally substituted methylthio, ethylthio, n-propylthio, isopropylthio, n-butylthio, isobutylthio, sec-butylthio and tert-butylthio.

Optionally substituted alkoxycarbonyl on its own or as a constituent of a radical in the general formulae denotes straight-chain or branched alkoxycarbonyl preferably having 1 to 6, in particular 1 to 4, carbon atoms. Examples which may be mentioned are optionally substituted methoxycarbonyl, ethoxycarbonyl, n-propoxycarbonyl, isopropoxycarbonyl, n-butoxycarbonyl, isobutoxycarbonyl, sec-butoxycarbonyl and tert-butoxycarbonyl.

Optionally substituted alkylcarbonyl on its own or as a constituent of a radical in the general formulae denotes straight-chain or branched alkylcarbonyl preferably having 1 to 6, in particular 1 to 4 carbon atoms. Examples which may be mentioned are optionally substituted methylcarbonyl, ethylcarbonyl, n-propylcarbonyl, isopropylcarbonyl, n-butylcarbonyl, isobutylcarbonyl, sec-butylcarbonyl and tert-butylcarbonyl.

Optionally substituted arylalkyl in the general formulae denotes arylalkyl, which is preferably optionally substituted in the aryl moiety and/or alkyl, preferably having 6 or 10, in particular 8, carbon atoms in the aryl moiety (preferably phenyl or naphthyl, in particular phenyl) and preferably 1 to 4, in particular 1 or 2, carbon atoms in the alkyl moiety, where the alkyl moiety can be straight-chain or branched. Optionally substituted benzyl and phenylethyl may be mentioned by way of example and preferably.

Optionally substituted hetaryl on its own or as a constituent of a radical in the general formulae denotes 5- to 7-membered rings preferably having 1 to 3, in particular 1 or 2, identical or different heteroaromatics. Heteroatoms in the heteroaromatics are oxygen, sulphur or nitrogen. Optionally substituted furyl, thienyl, pyrazolyl, imidazolyl, 1,2,3- and 1,2,4-triazolyl, isoxazolyl, thiazolyl, isothiazolyl, 1,2,3-, 1,3,4-, 1,2,4- and 1,2,5-oxadiazolyl, azepinyl, pyrrolyl, pyridyl, piperazinyl, pyridazinyl, pyrimidinyl, pyrazinyl, 1,3,5-, 1,2,4- and 1,2,3-triazinyl, 1,2,4-, 1,3,2-, 1,3,6- and 1,2,6-oxazinyl, oxepinyl, thiepinyl and 1,2,4-diazepinyl may be mentioned by way of example and preferably.

The optionally substituted radicals of the general formulae can carry one or more, preferably 1 to 3, in particular 1 to 2, identical or different substituents. Substituents which may be mentioned by way of example and preferably are:

alkyl preferably having 1 to 4, in particular 1 to 2 carbon atoms, such as methyl, ethyl, n-propyl, isopropyl, n-butyl, isobutyl, sec-butyl and tert-butyl; alkoxy preferably having 1 to 4, in particular 1 to 2 carbon atoms, such as methoxy, ethoxy, n-propoxy, isopropoxy, n-butoxy, isobutoxy, sec-butoxy and tert-butoxy; alkylthio such as methylthio, ethylthio, n-propylthio, isopropylthio, n-butylthio, isobutylthio, sec-butylthio and tert-butylthio; halogenoalkyl preferably having 1 to 4, in particular 1 to 2, carbon atoms and preferably 1 to 5, in particular 1 to 3, halogen atoms, where the halogen atoms are identical or different and, as halogen atoms, are preferably fluorine, chlorine or bromine, in particular fluorine or chlorine, such as difluoromethyl, trifluoromethyl, trichloromethyl; hydroxyl; halogen, preferably fluorine, chlorine, bromine and iodine, in particular fluorine and chlorine; cyano; nitro; amino; monoalkylamino and dialkylamino preferably having 1 to 4, in particular 1 or 2, carbon atoms per alkyl group, such as methylamino, methylethylamino, dimethylamino, n-propylamino, isopropylamino, methyl-n-butylamino; alkylcarbonyl radicals such as methylcarbonyl; alkoxycarbonyl preferably having 2 to 4, in particular 2 to 3, carbon atoms, such as methoxycarbonyl and ethoxycarbonyl; alkylsulphinyl having 1 to 4, in particular 1 to 2, carbon atoms; halogenosulphinyl having 1 to 4, in particular 1 to 2, carbon atoms and 1 to 5 halogen atoms, such as trifluoromethylsilfinyl; sulphonyl (—SO$_2$—OH); alkylsulphonyl preferably having 1 to 4, in particular 1 or 2, carbon atoms, such as methylsulphonyl and ethylsulphonyl or halogenoalkylsulphonyl having 1 to 4, in particular 1 to 2, carbon atoms and 1 to 5 halogen atoms such as trifluoromethylsulphonyl.

Possible suitable cyclic amino groups are heteroaromatic or aliphatic ring systems having one or more nitrogen atoms as heteroatom, in which the heterocycles can be saturated or unsaturated, a ring system or several fused ring systems, and optionally contain other heteroatoms such as nitrogen, oxygen and sulphur etc. Additionally, cyclic amino groups can also denote a spiro ring or a bridged ring system. The number of atoms which form cyclic amino groups is not restricted, for example in the case of a single ring system they consist of 3 to 8 atoms and in the case of a three-ring system of 7 to 11 atoms.

Examples of cyclic amino groups which may be mentioned are saturated and unsaturated monocyclic ring systems having a nitrogen atom as heteroatom, such as 1-azetidinyl, pyrrolidino, 2-pyrrolin-1-yl, 1-pyrrolyl, piperidino, 1,4-dihydropyridin-1-yl, 1,2,5,6-tetrahydropyridin-1-yl, homopiperidino; examples of cyclic amino groups which may be mentioned are saturated and unsaturated monocyclic ring systems having 2 or more nitrogen atoms as heteroatoms such as 1-imidazolidinyl, 1-imidazolyl, 1-pyrazolyl, 1-triazolyl, 1-tetrazolyl, 1-piperazinyl, 1-homopiperazinyl, 1,2-dihydropyridazin-1-yl, 1,2-dihydropropyrimidin-1-yl, perhydropyrimidin-1-yl and 1,4-diazacycloheptan-1-yl; examples of cyclic amino groups which may be mentioned are saturated and unsaturated monocyclic ring systems having 1 to 3 nitrogen atoms and 1 to 2 oxygen atoms as heteroatoms, such as oxazolidin-3-yl, isoxazolid-2-yl, morpholino or 2,6-dimethylmorpholino; examples of cyclic amino groups which may be mentioned are saturated and unsaturated monocyclic ring systems having 1 to 3 nitrogen atoms and 1 to 2 sulphur atoms as heteroatoms, examples of cyclic amino groups which may be mentioned are saturated and unsaturated fused cyclic ring systems such as indol-1-yl, 1,2-dihydrobenzimidazol-1-yl, perhydropyrrolo-[1,2-a]pyrazin-2-yl; examples of cyclic amino groups which may be mentioned are spirocyclic ring systems such as 2-azaspiro[4,5]-decan-2-yl; examples of cyclic amino groups which may be mentioned are bridged heterocyclic ring systems such as 2-azabicyclo[2.2.1]heptan-7-yl.

The substituted aryllactic acid-containing cyclodepsipeptides having 24 ring atoms which can be prepared according to the invention are generally defined by the general formula (I)

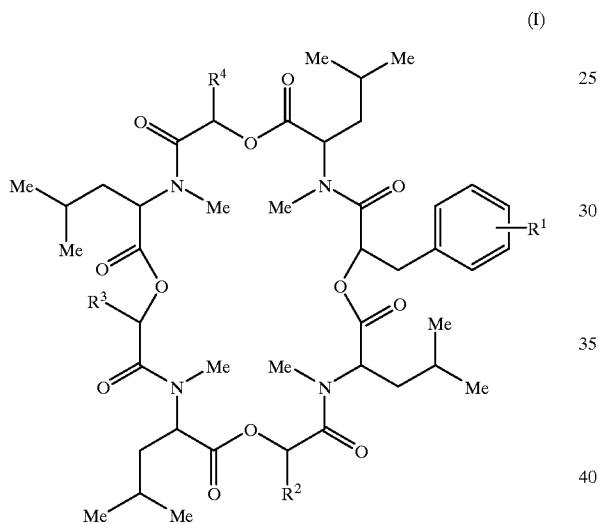

(I)

Preferably prepared compounds of the general formula (I) are those
in which
$R^1$ represents straight-chain or branched alkyl having up to 4 carbon atoms, in particular methyl, ethyl, propyl, isopropyl, butyl, isobutyl, sec-butyl, tert-butyl, cyclic alkyl having up to 6 carbon atoms, in particular cyclopropyl, cyclobutyl, cyclopentyl, cyclohexyl, alkoxy, in particular methoxy, ethoxy, propoxy, isopropoxy, butoxy, isobutoxy, sec-butoxy, tert-butoxy, cycloalkoxy, in particular cyclopropyloxy, alkenyloxy, in particular allyloxy, dioxoalkylene, in particular dioxomethylene, alkylamino, in particular methylamino, ethylamino, dialkylamino, in particular dimethylamino, diethylamino, alkoxycarbonyl, in particular methoxycarbonyl, ethoxycarbonyl, tert-butoxycarbonyl, alkylaminocarbonyl, in particular methylaminocarbonyl, dialkylaminocarbonyl, in particular dimethylaminocarbonyl, alkylaminosulphonyl, in particular methylaminosulphonyl, dialkylaminosulphonyl, in particular dimethylaminosulphonyl, alkylthio, in particular methylthio or tert-butylthio, alkylsulphinyl, in particular methylsulphinyl or tert-butylsulphinyl, alkylsulphonyl, in particular methysulphonyl or tert-butylsulphonyl, heteroarylsulphonyl, in particular N-morpholinosulphonyl or N-pyrazolylsulphonyl, each of which can be optionally substituted, hydroxyl, halogen, in particular bromine, chlorine, fluorine or iodine, nitro, amino, carboxyl, carbamoyl, cyano or, if appropriate, substituted cyclic amino groups, in particular N-pyrrolidino, N-piperidino, N-morpholino, N-(2,6-dimethyl-morpholino), N-methylpiperazino, N-thiomorpholino or N-dioxothiomorpholino, and $R^2$ and $R^4$ represent straight-chain or branched alkyl having up to 4 carbon atoms, in particular methyl, and $R^3$ represents represents straight-chain or branched alkyl having up to 4 carbon atoms, in particular methyl, or represents a benzyl radical which is optionally substituted by radicals from the series consisting of hydrogen, straight-chain or branched alkyl having up to 4 carbon atoms, in particular methyl, ethyl, propyl, isopropyl, butyl, isobutyl, sec-butyl, tert-butyl, cyclic alkyl having up to 6 carbon atoms, in particular cyclopropyl, cyclobutyl, cyclopentyl, cyclohexyl, alkoxy, in particular methoxy, ethoxy, propoxy, isopropoxy, butoxy, isobutoxy, sec-butoxy, tert-butoxy, cycloalkoxy, in particular cyclopropyloxy, alkenyloxy, in particular allyloxy, dioxoalkylene, in particular dioxomethylene, alkylamino, in particular methylamino, ethylamino, dialkylamino, in particular dimethyl-amino, diethylamino, alkoxycarbonyl, in particular methoxycarbonyl, ethoxy-carbonyl, tert-butoxycarbonyl, alkylaminocarbonyl, in particular methylamino-carbonyl, dialkylaminocarbonyl, in particular dimethylaminocarbonyl, alkylaminosulphonyl, in particular methylaminosulphonyl, dialkylaminosulphonyl, in particular dimethylaminosulphonyl, alkylthio, in particular methylthio or tert-butylthio, alkylsulphinyl, in particular methylsulphinyl or tert-butylsulphinyl, alkylsulphonyl, in particular methysulphonyl or tert-butylsulphonyl, heteroarylsulphonyl, in particular N-morpholinosulphonyl or N-pyrazolylsulphonyl, each of which can optionally be substituted, hydroxyl, halogen, in particular bromine, chlorine, fluorine or iodine, nitro, amino, carboxyl, carbamoyl, cyano, or which is optionally substituted by a suitable cyclic amino group, in particular N-pyrrolidino, N-piperidino, N-morpholino, N-(2,6-dimethylmorpholino), N-methylpiperazino, N-thiomorpholino or N-dioxothiomorpholino, with the exception of the compounds of the formula (I) in which $R^1$ represents 4-hydroxy, $R^3$ represents unsubstituted benzyl and the other radicals have the abovementioned meanings.

Particularly preferred prepared compounds of the general formula (I) are those
in which
$R^1$ represents alkoxy, in particular methoxy, ethoxy, propoxy, isopropoxy, butoxy, isobutoxy, sec-butoxy, tert-butoxy, alkylamino, in particular methylamino, ethylamino, dialkylamino, in particular dimethylamino, diethylamino, hydroxyl, halogen, in particular bromine, chlorine, fluorine or iodine, nitro, amino, if appropriate, substituted cyclic amino groups, in particular N-morpholino, N-methylpiperazino or N-dioxothiomorpholino, and $R^2$ and $R^4$ represent straight-chain or branched alkyl having up to 4 carbon atoms, in particular methyl, and R³ represents represents straight-chain or branched alkyl having up to 4 carbon atoms, in particular methyl, or represents a benzyl radical which is optionally substituted by radicals from the series consisting of hydrogen, alkoxy, in particular methoxy, ethoxy, propoxy, isopropoxy, butoxy, isobutoxy, sec-butoxy, tert-butoxy, alkylamino, in particular methylamino, ethylamino, dialkylamino, in particular dimethylamino, diethylamino, hydroxyl, halogen, in particular bromine, chlorine, fluorine or iodine, nitro, amino, or which is optionally substituted by a suitable cyclic amino group, in particular N-morpholino, N-methylpiperazino or N-dioxothiomorpholino, with the exception of the compounds of the formula (I) in which R¹ represents 4-hydroxy,
R³ represents unsubstituted benzyl and the other radicals have the meaning given above.

Very particularly preferred compounds of the general formula (I) prepared are those
in which R¹ represents alkoxy, in particular methoxy, tert-butoxy, hydroxyl, halogen, in particular bromine, chlorine, fluorine or iodine, nitro, amino, dialkylamino, in particular dimethylamino, or, if appropriate, substituted cyclic amino groups, in particular N-morpholino, and R² and R⁴ represent methyl, and R³ represents represents a benzyl radical which is optionally substituted by radicals from the series consisting of hydrogen, alkoxy, in particular methoxy, tert-butoxy, hydroxyl, halogen, in particular bromine, chlorine, fluorine or iodine, nitro, amino, dialkylamino, in particular dimethylamino, or which is optionally substituted by a suitable cyclic amino group, in particular N-morpholino, with the exception of the compounds of the formula (I) in which R¹ represents 4-hydroxyl,
R³ represents unsubstituted benzyl and the other radicals have the meaning given above.

Under the preparation conditions according to the invention, the optically active, stereoisomeric forms of the compounds of the general formula (I) are formed.

Preferably, however, compounds of the general formula (I) are formed in which the α-amino acids have an (S)-configuration (L-form) and the 2-hydroxy-carboxylic acids have an (R)-configuration (D-form).

In detail, the following optically active compounds of the general formula (I) may be mentioned:

Cyclo(-N-methyl-L-leucyl-D-4-nitro-phenyllactyl-N-methyl-L-leucyl-D-lactyl-N-methyl-L-leucyl-D-lactyl-N-methyl-L-leucyl-D-lactyl-)
Cyclo(-N-methyl-L-leucyl-D-4-nitro-phenyllactyl-N-methyl-L-leucyl-D-lactyl-N-methyl-L-leucyl-D-phenyllactyl-N-methyl-L-leucyl-D-lactyl-)
Cyclo(-N-methyl-L-leucyl-D-4-nitro-phenyllactyl-N-methyl-L-leucyl-D-lactyl-N-methyl-L-leucyl-D-4-nitro-phenyllactyl-N-methyl-L-leucyl-D-lactyl-)
Cyclo(-N-methyl-L-leucyl-D-3-nitro-phenyllactyl-N-methyl-L-leucyl-D-lactyl-N-methyl-L-leucyl-D-lactyl-N-methyl-L-leucyl-D-lactyl-)
Cyclo(-N-methyl-L-leucyl-D-3-nitro-phenyllactyl-N-methyl-L-leucyl-D-lactyl-N-methyl-L-leucyl-D-phenyllactyl-N-methyl-L-leucyl-D-lactyl-)
Cyclo(-N-methyl-L-leucyl-D-3-nitro-phenyllactyl-N-methyl-L-leucyl-D-lactyl-N-methyl-L-leucyl-D-3-nitro-phenyllactyl-N-methyl-L-leucyl-D-lactyl-)
Cyclo(-N-methyl-L-leucyl-D-2-nitro-phenyllactyl-N-methyl-L-leucyl-D-lactyl-N-methyl-L-leucyl-D-lactyl-N-methyl-L-leucyl-D-lactyl-)
Cyclo(-N-methyl-L-leucyl-D-2-nitro-phenyllactyl-N-methyl-L-leucyl-D-lactyl-N-methyl-L-leucyl-D-phenyllactyl-N-methyl-L-leucyl-D-lactyl-)
Cyclo(-N-methyl-L-leucyl-D-2-nitro-phenyllactyl-N-methyl-L-leucyl-D-lactyl-N-methyl-L-leucyl-D-2-nitro-phenyllactyl-N-methyl-L-leucyl-D-lactyl-)
Cyclo(-N-methyl-L-leucyl-D-4-amino-phenyllactyl-N-methyl-L-leucyl-D-lactyl-N-methyl-L-leucyl-D-lactyl-N-methyl-L-leucyl-D-lactyl-)
Cyclo(-N-methyl-L-leucyl-D-4-amino-phenyllactyl-N-methyl-L-leucyl-D-lactyl-N-methyl-L-leucyl-D-phenyllactyl-N-methyl-L-leucyl-D-lactyl-)
Cyclo(-N-methyl-L-leucyl-D-4-amino-phenyllactyl-N-methyl-L-leucyl-D-lactyl-N-methyl-L-leucyl-D-4-amino-phenyllactyl-N-methyl-L-leucyl-D-lactyl)
Cyclo(-N-methyl-L-leucyl-D-3-amino-phenyllactyl-N-methyl-L-leucyl-D-lactyl-N-methyl-L-leucyl-D-lactyl-N-methyl-L-leucyl-D-lactyl-)
Cyclo(-N-methyl-L-leucyl-D-3-amino-phenyllactyl-N-methyl-L-leucyl-D-lactyl-N-methyl-L-leucyl-D-phenyllactyl-N-methyl-L-leucyl-D-lactyl-)
Cyclo(-N-methyl-L-leucyl-D-3-amino-phenyllactyl-N-methyl-L-leucyl-D-lactyl-N-methyl-L-leucyl-D-3-amino-phenyllactyl-N-methyl-L-leucyl-D-lactyl) methyl-L-leucyl-D-lactyl-N-methyl-L-leucyl-D-lactyl-)
Cyclo(-N-methyl-L-leucyl-D-2-amino-phenyllactyl-N-methyl-L-leucyl-D-lactyl-N-methyl-L-leucyl-D-phenyllactyl-N-methyl-L-leucyl-D-lactyl-)
Cyclo(-N-methyl-L-leucyl-D-2-amino-phenyllactyl-N-methyl-L-leucyl-D-lactyl-N-methyl-L-leucyl-D-2-amino-phenyllactyl-N-methyl-L-leucyl-D-lactyl-)
Cyclo(-N-methyl-L-leucyl-D-4-amino-phenyllactyl-N-methyl-L-leucyl-D-lactyl-N-methyl-L-leucyl-D-Iactyl-N-methyl-L-leucyl-D-lactyl-)
Cyclo(-N-methyl-L-leucyl-D-4-hydrox-phenyllactyl-N-methyl-L-leucyl-D-lactyl-N-methyl-L-leucyl-D-4-hydroxy-phenyllactyl-N-methyl-L-leucyl-D-lactyl-)
Cyclo(-N-methyl-L-leucyl-D-3-hydroxy-phenyllactyl-N-methyl-L-leucyl-D-lactyl-N-methyl-L-leucyl-D-lactyl-N-methyl-L-leucyl-D-lactyl-)
Cyclo(-N-methyl-L-leucyl-D-3-hydroxy-phenyllactyl-N-methyl-L-leucyl-D-lactyl-N-methyl-L-leucyl-D-phenyllactyl-N-methyl-L-leucyl-D-lactyl-)
Cyclo(-N-methyl-L-leucyl-D-3-hydroxy-phenyllactyl-N-methyl-L-leucyl-D-lactyl-N-methyl-L-leucyl-D-3-hydroxy-phenyllactyl-N-methyl-L-leucyl-D-lactyl)
Cyclo(-N-methyl-L-leucyl-D-2-hydroxy-phenyllactyl-N-methyl-L-leucyl-D-lactyl-N-methyl-L-leucyl-D-lactyl-N-methyl-L-leucyl-D-lactyl-)
Cyclo(-N-methyl-L-leucyl-D-2-hydroxy-phenyllactyl-N-methyl-L-1eucyl-D-lactyl-N-methyl-L-leucyl-D-phenyllactyl-N-methyl-L-leucyl-D-lactyl-)
Cyclo(-N-methyl-L-leucyl-D-2-amino-phenyllactyl-N-methyl-L-leucyl-D-lactyl-N-methyl-L-leucyl-D-2-hydroxy-phenyllactyl-N-methyl-L-leucyl-D-lactyl-)
Cyclo(-N-methyl-L-leucyl-D-4-amino-phenyllactyl-N-methyl-L-leucyl-D-lactyl-N-methyl-L-leucyl-D-lactyl-N-methyl-L-leucyl-D-lactyl-)
Cyclo(-N-methyl-L-leucyl-D-4-amino-phenyllactyl-N-methyl-L-leucyl-D-lactyl-N-methyl-L-leucyl-D-phenyllactyl-N-methyl-L-leucyl-D-lactyl-)
Cyclo(-N-methyl-L-leucyl-D-4-amino-phenyllactyl-N-methyl-L-leucyl-D-lactyl-N-methyl-L-leucyl-D-4-methoxy-phenyllactyl-N-methyl-L-leucyl-D-lactyl)

Cyclo(-N-methyl-L-leucyl-D-3-methoxy-phenyllactyl-N-methyl-L-leucyl-D-lactyl-N-methyl-L-leucyl-D-lactyl-N-methyl-L-leucyl-D-lactyl-)

Cyclo(-N-methyl-L-leucyl-D-2-hydroxy-phenyllactyl-N-methyl-L-leucyl-D-lactyl-N-methyl-L-leucyl-D-phenyllactyl-N-methyl-L-leucyl-D-lactyl-)

Cyclo(-N-methyl-L-leucyl-D-3-methoxy-phenyllactyl-N-methyl-L-leucyl-D-lactyl-N-methyl-L-leucyl-D-3-methoxy-phenyllactyl-N-methyl-L-leucyl-D-lactyl)

Cyclo(-N-methyl-L-leucyl-D-2-methoxy-phenyllactyl-N-methyl-L-leucyl-D-lactyl-N-methyl-L-leucyl-D-lactyl-N-methyl-L-leucyl-D-lactyl-)

Cyclo(-N-methyl-L-leucyl-D-2-methoxy-phenyllactyl-N-methyl-L-leucyl-D-lactyl-N-methyl-L-leucyl-D-phenyllactyl-N-methyl-L-leucyl-D-lactyl-)

Cyclo(-N-methyl-L-ieucyl-D-2-methoxy-phenyllactyl-N-methyl-L-leucyl-D-lactyl-N-methyl-L-leucyl-D-2-methoxy-phenyllactyl-N-methyl-L-leucyl-D-lactyl-)

Cyclo(-N-methyl-L-leucyl-D-4-tert-butoxy-phenyllactyl-N-methyl-L-leucyl-D-lactyl-N-methyl-L-leucyl-D-lactyl-N-methyl-L-leucyl-D-lactyl-)

Cyclo(-N-methyl-L-leucyl-D-4-tert-butoxy-phenyllactyl-N-methyl-L-leucyl-D-lactyl-N-methyl-L-leucyl-D-phenyllactyl-N-methyl-L-leucyl-D-lactyl-)

Cyclo(-N-methyl-L-leucyl-D-4-tert-butoxy-phenyllactyl-N-methyl-L-1eucyl-D-lactyl-N-methyl-L-leucyl-D-4-tert-butoxy-phenyllactyl-N-methyl-L-leucyl-D-lactyl)

Cyclo(-N-methyl-L-leucyl-D-3-tert-butoxy-phenyllactyl-N-methyl-L-leucyl-D-lactyl-N-methyl-L-leucyl-D-lactyl-N-methyl-L-leucyl-D-lactyl-)

Cyclo(-N-methyl-L-leucyl-D-3-tert-butoxy-phenyllactyl-N-methyl-L-leucyl-D-lactyl-N-methyl-L-leucyl-D-phenyllactyl-N-methyl-L-leucyl-D-lactyl-)

Cyclo(-N-methyl-L-leucyl-D-3-tert-butoxy-phenyllactyl-N-methyl-L-leucyl-D-lactyl-N-methyl-L-leucyl-D-3-tert-butoxy-phenyllactyl-N-methyl-L-leucyl-D-lactyl)

Cyclo(-N-methyl-L-leucyl-D-2-tert-butoxy-phenyllactyl-N-methyl-L-leucyl-D-lactyl-N-methyl-L-leucyl-D-lactyl-N-methyl-L-leucyl-D-lactyl-)

Cyclo(-N-methyl-L-leucyl-D-2-tert-butoxy-phenyllactyl-N-methyl-L-leucyl-D-lactyl-N-methyl-L-leucyl-D-phenyllactyl-N-methyl-L-leucyl-D-lactyl-)

Cyclo(-N-methyl-L-ieucyl-D-2-tert-butoxy-phenyllactyl-N-methyl-L-leucyl-D-lactyl-N-methyl-L-leucyl-D-2-tert-butoxy-phenyllactyl-N-methyl-L-leucyl-D-lactyl-)

Cyclo(-N-methyl-L-leucyl-D-4-N-morpholino-phenyllactyl-N-methyl-L-leucyl-D-lactyl-N-methyl-L-leucyl-D-lactyl-N-methyl-L-leucyl-D-lactyl-)

Cyclo(-N-methyl-L-leucyl-D-4-N-morpholino-phenyllactyl-N-methyl-L-leucyl-D-lactyl-N-methyl-L-leucyl-D-phenyllactyl-N-methyl-L-leucyl-D-lactyl-)

Cyclo(-N-methyl-L-leucyl-D-4-N-morpholino-phenyllactyl-N-methyl-L-leucyl-D-lactyl-N-methyl-L-leucyl-D-4-N-morpholino-phenyllactyl-N-methyl-L-leucyl-D-lactyl)

Cyclo(-N-methyl-L-leucyl-D-3-N-morpholino-phenyllactyl-N-methyl-L-leucyl-D-lactyl-N-methyl-L-leucyl-D-lactyl-N-methyl-L-leucyl-D-lactyl-)

Cyclo(-N-methyl-L-leucyl-D-3-amino-phenyllactyl-N-methyl-L-leucyl-D-lactyl-N-N-methyl-L-leucyl-D-phenyllactyl-N-methyl-L-leucyl-D-lactyl-)

Cyclo(-N-methyl-L-leucyl-D-2-N-morpholino-phenyllactyl-N-methyl-L-leucyl-D-lactyl-N-methyl-L-leucyl-D-lactyl-N-methyl-L-leucyl-D-lactyl-)

Cyclo(-N-methyl-L-leucyl-D-3-N-morpholino-phenyllactyl-N-methyl-L-leucyl-D-lactyl-N-methyl-L-leucyl-D-phenyllactyl-N-methyl-L-leucyl-D-lactyl-)

Cyclo(-N-methyl-L-leucyl-D-2-N-morpholino-phenyllactyl-N-methyl-L-leucyl-D-lactyl-N-methyl-L-leucyl-D-2-N-morpholino-phenyllactyl-N-methyl-L-leucyl-D-lactyl-)

Cyclo(-N-methyl-L-leucyl-D-2-amino-phenyl-lactyl-N-methyl-L-leucyl-D-lactyl-N-morpholino-phenyllactyl-N-methyl-L-leucyl-D-lactyl-)

Cyclo(-N-methyl-L-leucyl-D-4-dimethylamino-phenyllactyl-N-methyl-L-leucyl-D-lactyl-N-methyl-L-leucyl-D-lactyl-N-methyl-L-leucyl-D-lactyl-)

Cyclo(-N-methyl-L-leucyl-D-4-dimethylamino-phenyllactyl-N-methyl-L-leucyl-D-lactyl-N-methyl-L-leucyl-D-phenyllactyl-N-methyl-L-leucyl-D-lactyl-)

Cyclo(-N-methyl-L-leucyl-D-4-dimethylamino-phenyllactyl-N-methyl-L-leucyl-D-lactyl-N-methyl-L-leucyl-D-4-dimethylamino-phenyllactyl-N-methyl-L-leucyl-D-lactyl)

Cyclo(-N-methyl-L-leucyl-D-3-dimethylamino-phenyllactyl-N-methyl-L-leucyl-D-lactyl-N-methyl-L-leucyl-D-lactyl-N-methyl-L-leucyl-D-lactyl-)

Cyclo(-N-methyl-L-leucyl-D-3-dimethylamino-phenyllactyl-N-methyl-L-leucyl-D-lactyl-N-methyl-L-leucyl-D-phenyllactyl-N-methyl-L-leucyl-D-lactyl-)

Cyclo(-N-methyl-L-leucyl-D-3-dimethylamino-phenyllactyl-N-methyl-L-leucyl-D-lactyl-N-methyl-L-leucyl-D-lactyl-N-methyl-L-leucyl-D-lactyl-)

Cyclo(-N-methyl-L-leucyl-D-2-dimethylamino-phenyllactyl-N-methyl-L-leucyl-D-lactyl-N-methyl-L-leucyl-D-phenyllactyl-N-methyl-L-leucyl-D-lactyl-)

Cyclo(-N-methyl-L-leucyl-D-2-dimethylamino-phenyllactyl-N-methyl-L-leucyl-D-lactyl-N-methyl-L-leucyl-D-2-dimethylamino-phenyllactyl-N-methyl-L-leucyl-D-lactyl-)

Cyclo(-N-methyl-L-leucyl-D-4-dimethylamino-phenyllactyl-N-methyl-L-leucyl-D-lactyl-leucyl-D-lactyl-N-methyl-L-leucyl-D-lactyl-)

Cyclo(-N-methyl-L-leucyl-D-4-idimtyaiophenyllactyl-N-methyl-L-leucyl-D-lactyl-N-ethy-leucyl-D--phenyllactyl-N-methyl-L-Ieucyl-D-lactyl-)

Cyclo(-N-methyl-L-leucyl-D4-iodphenyllactyl-N-methyl-L-leucyl-D-lactyl-N-methyl-L-leucyl-D4-iodphenyllactyl-N-methyl-L-leucyl-D-lactyl)

Cyclo(-N-methyl-L-leucyl-D-3-iodphenyllactyl-N-methyl-L-leucyl-D-lactyl-N-methyl-L-leucyl-D-lactyl-N-methyl-L-leucyl-D-lactyl-)

Cyclo(-N-methyl-L-leucyl-D-3-iodphenyllactyl-N-methyl-L-leucyl-D-lactyl-N-methyl-L-leucyl-D-phenyllactyl-N-methyl-L-leucyl-D-lactyl-)

Cyclo(-N-methyl-L-leucyl-D-3-iodphenyllactyl-N-methyl-L-leucyl-D-lactyl-N-methyl-L-leucyl-D-3-iodphenyllactyl-N-methyl-L-leucyl-D-lactyl)

Cyclo(-N-methyl-L-leucyl-D-2-iodphenyllactyl-N-methyl-L-leucyl-D-lactyl-N-methyl-L-leucyl-D-lactyl-N-methyl-L-leucyl-D-lactyl-)

Cyclo(-N-methyl-L-leucyl-D-2-iodphenyllactyl-N-methyl-L-leucyl-D-lactyl-N-methyl-L-leucyl-D-phenyllactyl-N-methyl-L-leucyl-D-lactyl-)

Cyclo(-N-methyl-L-leucyl-D-2-iodphenyllactyl-N-methyl-L-leucyl-D-lactyl-N-methyl-L-leucyl-D-2-iodphenyllactyl-N-methyl-L-leucyl-D-lactyl-)

Cyclo(-N-methyl-L-leucyl-D-4-bromphenyllactyl-N-methyl-L-leucyl-D-lactyl-N-methyl-L-leucyl-D-lactyl-N-methyl-L-leucyl-D-lactyl-)

Cyclo(-N-methyl-L-leucyl-D-4-bromphenyllactyl-N-methyl-L-leucyl-D-lactyl-N-methyl-L-leucyl-D-phenyllactyl-N-methyl-L-leucyl-D-lactyl-)

Cyclo(-N-methyl-L-leucyl-D-4-bromphenyllactyl-N-methyl-L-leucyl-D-lactyi-N-methyl-L-leucyl-D-4-bromphenyllactyl-N-methyl-L-leucyl-D-lactyl)

Cyclo(-N-methyl-L-leucyl-D-3-bromphenyllactyl-N-methyl-L-leucyl-D-lactyl-N-methyl-L-leucyl-D-lactyl-N-methyl-L-leucyl-D-lactyl-)

Cyclo(-N-methyl-L-leucyl-D-3-bromphenyllactyl-N-methyl-L-leucyl-D-lactyl-N-methyl-L-leucyl-D-phenyllactyl-N-methyl-L-leucyl-D-lactyl-)

Cyclo(-N-methyl-L-leucyl-D-3-bromphenyllactyl-N-methyl-L-leucyl-D-lactyl-N-methyl-L-leucyl-D-3-bromphenyllactyl-N-methyl-L-leucyl-D-lactyl)

Cyclo(-N-methyl-L-leucyl-D-2-bromphenyllactyl-N-methyl-L-leucyl-D-lactyl-N-methyl-L-leucyl-D-lactyl-N-methyl-L-leucyl-D-lactyl-)

Cyclo(-N-methyl-L-leucyl-D-2-bromphenyllactyl-N-methyl-L-leucyl-D-lactyl-N-methyl-L-leucyl-D-phenyllactyl-N-methyl-L-leucyl-D-lactyl-)

Cyclo(-N-methyl-L-leucyl-D-2-bromphenyllactyl-N-methyl-L-leucyl-D-lactyl-N-methyl-L-leucyl-D-2-bromphenyllactyl-N-methyl-L-leucyl-D-lactyl-)

Cyclo(-N-methyl-L-leucyl-D-4-chlorphenyllactyl-N-methyl-L-leucyl-D-lactyl-N-methyl-L-leucyl-D-lactyl-N-methyl-L-leucyl-D-lactyl-)

Cyclo(-N-methyl-L-leucyl-D-4-chlorphenyllactyl-N-methyl-L-leucyl-D-lactyl-N-methyl-L-leucyl-D-phenyllactyl-N-methyl-L-leucyl-D-lactyl-)

Cyclo(-N-methyl-L-leucyl-D-4-chlorphenyllactyl-N-methyl-L-leucyl-D-lactyl-N-methyl-L-leucyl-D-4-chlorphenyllactyl-N-methyl-L-leucyl-D-lactyl)

Cyclo(-N-methyl-L-leucyl-D-3-chlorphenyllactyl-N-methyl-L-leucyl-D-lactyl-N-methyl-L-leucyl-D-lactyl-N-methyl-L-leucyl-D-lactyl-)

Cyclo(-N-methyl-L-leucyl-D-3-chlorphenyllactyl-N-methyl-L-leucyl-D-lactyl-N-methyl-L-leucyl-D-phenyllactyl-N-methyl-L-leucyl-D-lactyl-)

Cyclo(-N-methyl-L-leucyl-D-3-chlorphenyllactyl-N-methyl-L-leucyl-D-lactyl-N-methyl-L-leucyl-D-3-chlorphenyllactyl-N-methyl-L-leucyl-D-lactyl)

Cyclo(-N-methyl-L-leucyl-D-2-chlorphenyllactyl-N-methyl-L-leucyl-D-lactyl-N-methyl-L-leucyl-D-lactyl-N-methyl-L-leucyl-D-lactyl-)

Cyclo(-N-methyl-L-leucyl-D-2-bromphenyllactyl-N-methyl-L-leucyl-D-lactyi-N-methyl-L-leucyl-D-phenyllactyl-N-methyl-L-leucyl-D-lactyl-)

Cyclo(-N-methyl-L-leucyl-D-2-chlorphenyllactyl-N-methyl-L-leucyl-D-lactyl-N-methyl-L-leucyl-D-2-chlorphenyllactyl-N-methyl-L-leucyl-D-lactyl-)

The compounds of the general formula (I) are known in some cases (cf. e.g.: WO 94/19334; WO 95/19053: EP-OS [European Published Specification] 626 375; EP-OS [European Published Specification] 626 376).

If, in process a according to the invention for the preparation of the substituted aryllactic acid-containing cycodepsipeptides having 24 ring atoms (I) 4-nitrophenyl-aanine ($R^1$=4-$NO_2$) is employed as amino acids of the formula (II), the process can thus be represented. for example, by the following reaction scheme:

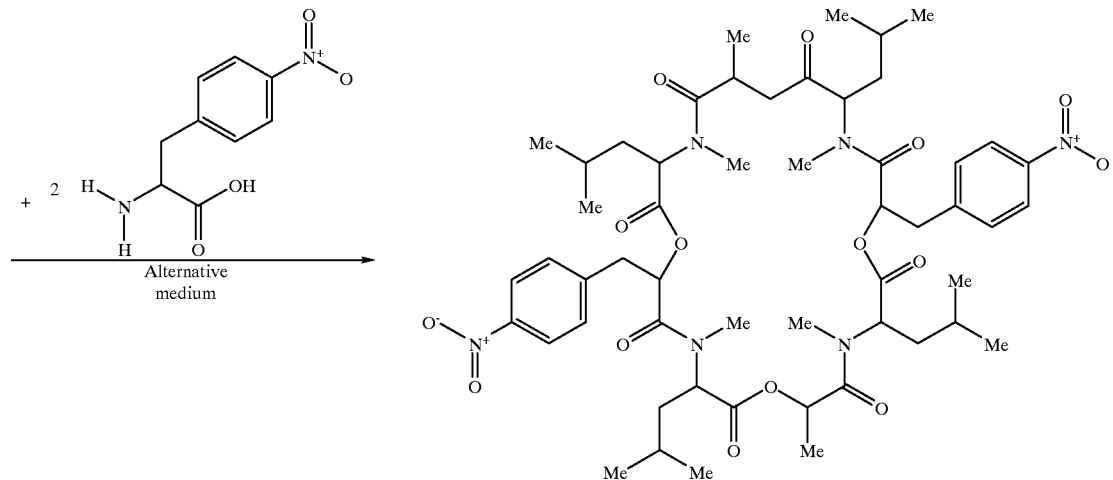

Formulae (II) to (V) provide a general definition of the amino acids needed as starting substances for carrying out process a according to the invention. In these formulae, $R^1$, $R^2$ $R^3$ and $R^4$ preferably represent those radicals which have already been mentioned as preferred for these subsituents in connection with the description of the substances of the formula (I) according to the invention.

The natural or synthetic amino acids used as starting substances can, if they are chiral, be present in the (S)- or (R)-configuration (L- or D-form). However, β-amino acids having the (S)-configuration are preferred.

Examples which may be mentioned are:

Aad, Abu, jAbu, ABz, 2ABz, εAca, Ach, Acp, Adpd, Ahb, Aib, βAib, Ala, βAla, ΔAla, Alg, All, Ama, Amt, Ape, Apm, Apr, Arg, Asn, Asp, Asu, Aze, Azi, Bai, Bph, Can, Cit, Cys, (Cys)$_2$, Cyta, Daad, Dab, Dadd, Dap, Dapm, Dasu, Djen, Dpa, Dtc, Fel, Gln, Glu, Gly, Guv, hAla, hArg, hCys, hGln, hGlu, His, hule, hLeu, hLys, hMet, hPhe, hPro, hSer, hThr, hTrp, hTyr, Hyl, Hyp, 3Hyp, Ile, Ise, Iva, Kyn, Lant, Lcn, Leu, Lsg, Lys, βLys, ΔLys, Met, Mim, Min, nArg, Nle, Nva, Oly, Orn, Pan, Pec, Pen, Phe, Phg, Pic, Pro, ΔPro, Pse, Pse, Pya, Pyr, Pza, Qin, Ros, Sar, Sec, Sem, Ser, Thi, βThi, Thr, Thy, Thx, Tia, Tle, Tly, Trp, Trta, Tyr, Val, Nal, Tbg, Npg, Chg, Thia (cf. e.g. Houben-Weyl, Methoden der Organischen Chemie [Methods of Organic Chemistry], Volume XV/1 and 2, Stuttgart, 1974).

Preferably, however, substituted phenylalanines (Phe) may be mentioned. In the substituted phenylalanines of the general formula (II), $R^1$ preferably represents the radical which has already been mentioned as preferred for this substituent in connection with the description of the substances of the formula (I) according to the invention.

If, in process b according to the invention for the preparation of the substituted aryllactic acid-containing cyclodepsipeptides having 24 ring atoms (I), 4-nitrophenyl-lactic acid ($R^1$=4-$NO_2$) is employed as 2-hydroxy-carboxylic acids of the formula (VI) process b can thus be represented, for example, by the following reaction scheme:

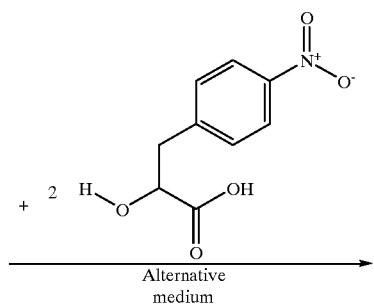
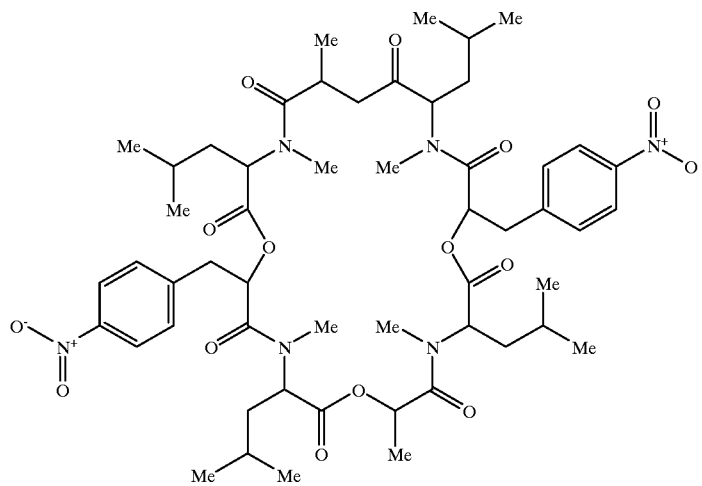

Formulae (VI) to (IX) provide a general definition of the 2-hydroxy-carboxylic acids needed as starting substances for carrying out process b according to the invention.

In these formulae, $R^1$, $R^2$, $R^3$ and $R^4$ preferably represent those radicals which have already been mentioned as preferred for these substituents in connection with the description of the substances of the formula (I) according to the invention.

The 2-hydroxy-carboxylic acids used as starting substances, if they are chiral, can be present in the (S)- or (R)-configuration (L- or D-form). However, the 2-hydroxy-carboxylic acids having the (S)-configuration are preferred.

Examples which may be mentioned are:

Hyac, Hyba, Hydd, Hyde, Hyic, Hyiv, Hymb, Hypp, Hypr (Lac), Hytd, Hyud, Hyva, PhLac (cf. e.g. Houben-Weyl, Methoden der Organischen Chemie [Methods of Organic Chemistry], Volume XV/1 and 2, Stuttgart, 1974).

Preferably, however, substituted phenyllactic acids (PhLac) may be mentioned. In the substituted phenyllactic acids of the general formula (VI) $R^1$ is preferably the radical which has already been mentioned as preferred for this substituent in connection with the description of the substances of the formula (I) according to the invention.

A suitable fungal s train which may be mentioned for carrying out both processes a and b according to the invention is Mycelia sterilia of the species Agonomycetales.

In particular, the fungal strain Mycelia sterilia 541-11 deposited on 30.11.1995 under the number DSM 10 345 in the German Collection for Microorganisms (DMS) in Brunswick in accordance with the Budapest Convention may be mentioned.

The process can also be carried out with synthetases isolated from microorganisms. The cyclodepsipeptide synthetases needed for this can be isolated from the fungal strain mentioned above by processes known from the literature (cf. e.g. Isolation of enniatin synthetases: R. Pieper, H. Kleinkauf, R. Zocher, J. Antibiotics 45, 1993, pp. 1273–1277; DE-A 4 406 025).

The fermentation of the fungal strains of the species Agonomycetales is carried out by methods known per se in the presence of suitable nutrient solutions. These nutrient solutions contain the salts and also carbon and nitrogen sources necessary for the growth of the fungi.

Possible suitable organic salts for carrying out the process according to the invention are all alkali metal, alkaline earth metal and metal salts of elements of subgroup II to VIII of the Periodic Table.

Examples which may be mentioned of these are the acetates, chlorides, bromides, iodides, fluorides, nitrates, nitrites, phosphates, hydrogenphosphates, dihydrogenphosphates, phosphites, hydrogenphosphites, sulfates, hydrogensulfates, sulfites, hydrogensulfites, carbonates and hydrogencarbonates of lithium, sodium, potassium, caesium, magnesium, calcium, barium, zinc, cadmium, scandium, titanium, zirconium, vanadium, niobium, chromium, molybdenum, manganese, iron, cobalt or nickel.

Preferably, the acetates, halides, phosphates, hydrogenphosphates, dihydrogen-phosphates, and nitrates of the alkaline earth metals are used, in particular magnesium, and metals of subgroup II, VII and VIII of the Periodic Table, for example zinc, manganese and iron.

Possible carbon sources for carrying out the process according to the invention are carbohydrates and carbohydrate-containing products.

Examples which may be mentioned of these are the monosaccharides, such as pentoses, in particular ribose, the hexoses, in particular glucose and fructose, the oligosaccharides such as disaccharides, in particular sucrose, maltose and lactose, the trisaccharides, in particular raffinose, and also the tetra-, penta- and hexasaccharides.

Preferably, monosaccharides such as hexoses, in particular glucose, and oligosaccharides such as disaccharides, in particular sucrose, are used.

Possible nitrogen sources for carrying out the process according to the invention are amino acids and nitrogen-containing salts.

Examples which may be mentioned of these are the natural and synthetic amino acids above or nitrogen-containing salts such as ammonium nitrate, ammonium nitrite or nitrates and nitrites of the metals mentioned above.

Preferably, the natural amino acids mentioned above and also nitrogen-containing salts such as ammonium nitrate are used.

The fungal strains used for the fermentative process are first cultivated by methods known per se in a medium consisting, for example, of molasses/cornsteep liquor. After cultivation has taken place, the mycelium is isolated. For the preparation of the free culture, a Fusarium-defined medium (FDM), consisting of a carbon source and inorganic salts, is inoculated with mycelium and again fermented. After a few days, the FDM main culture can be prepared by "überimpten" of 1 ml each of preculture and fermented analogously.

The actual fermentation is then carried out in the presence of compounds of the formulae (II) to (V) or (VI) to (IX).

The fermentation period is 1 to 30 days. The fermentation is carried out at temperatures between +5° C. and +40° C., preferably between +15° C. and +35° C., particularly prefer between +25° C. and +30° C. It is carried out under sterile conditions and at normal pressure.

For carrying out the fermentation, the compounds of the formulae (II) to (V) or (VI) to (IX) are in general employed in a concentration of 5 mM to 100 mM, preferably 5 mM to 70 mM.

After fermentation is complete, the mycelium is removed from the culture, and the filtrate is optionally extracted several times with an organic solvent, homogenized and then filtered. The culture filtrate obtained is extracted in the customary manner, dried and concentrated in vacuo.

The cyclodepsipeptide crude products obtained can be purified in a customary manner by column chromatography or by countercurrent distribution. Which is the optimum process must be decided from case to case (cf. also the Preparation Examples).

If the process according to the invention is carried out in the presence of isolated cyclodepsipeptide synthetases, it is carried out in an aqueous buffer system in the presence of metal salts, S-adenosyl-L-methionine (SAM) and adenosine triphosphate (ATP).

Metal salts which may be mentioned are: acetates, chlorides, bromides, iodides, fluorides, nitrates, phosphates, hydrogenphosphates, phosphites, hydrogenphosphites, sulfates, hydrogen sulfates, sulfites, hydrogensulfites, carbonates and hydrogencarbonates of lithium, sodium, potassium, caesium. magnesium, calcium or barium.

Preferably, alkaline earth metal salts are used, for example magnesium fluoride, sulfate or acetate.

Processes a and b according to the invention are carried out in an aqueous buffer solution.

Examples which may be mentioned of this are commercially available buffer solutions, e.g. for pH 1.0, in particular glycine-hydrochloric acid, for pH 2.0 to 4.0, in particular citrate-hydrochloric acid, for pH 5.0 to 6.0, in particular citrate-sodium hydroxide solution, for pH 7.0, in particular phosphate, in particular borate-hydrochloric acid, and for pH 8.0, pH 9.0 to 10.0, in particular boric acid/potassium chloride-sodium hydroxide solution.

The processes are preferably carried out in the "physiological range", i.e. at a pH of 6.0 to 9.5 and a phosphate buffer solution is preferably used for this, in particular potassium hydrogen phosphate/disodium hydrogenphosphate or potassium hydrogenphosphate/dipotassium hydrogenphosphate.

For carrying out the process, in general 2 mM to 8 mM, preferably 3 mM to 5 mM of compounds of the formulae (II) to (V) or (VI) to (IX), S-adenosyl-L-methionine (SAM), 3 mM to 9 mM, preferably 4 mM to 6 mM of adenosine triphosphate (ATP), and 2 mM to 25 mM, preferably 5 mM to 15 mM of alkaline earth metal salt, 10 mM to 100 mM, preferably 40 mM to 60 mM of buffer are employed in vitro with 100 $\mu$g to 1000 pg, preferably 200 $\mu$g to 600 $\mu$g, of isolated cyclodepsipeptide synthetase.

The reaction time of the enzymatic in vitro synthesis is 2 minutes to 24 hours. The enzymatic in vitro synthesis is carried out in a temperature range from 0° C. to +50° C., preferably at +10° C. to +35° C., particularly preferably between +20° C. and +30° C.

It proceeds in a pH range from 6.5 to 9.5, preferably at 7.0 to 8.0, the pH being kept constant at 7.3 during the entire reaction by addition of a buffer.

Preferably, the process is carried out under sterile reaction conditions and at normal pressure.

The enzymatic in vitro synthesis can be stopped by addition of water.

If compounds of the formulae (II) to (V) are used, however, it is advantageous to carry out the enzymatic in vitro synthesis in the presence of the corresponding transaminases or dehydrogenases.

For working up, the aqueous phase is extracted several times with an organic solvent, dried and concentrated in vacuo.

The cyclodepsipeptide crude products obtained can be purified in a customary manner by column chromatography or by countercurrent distribution. Which is the optimum process must also be decided from case to case here (cf. also the Preparation Examples).

PREPARATION EXAMPLES

Example 1
Cyclo(-N-methyl-L-leucyl-D-lactyl-N-methiyl-L-leucyl-D-4-nitro-phenyllactyl-N-methy-L-leucyl-D-lactyl-N-methyl-L-leucyl-D-4-tnirt-phenyllactyl-)

The products obtained by processes a and b are purified by means of preparative HPLC (RP-18/acetonitrile-water)

$^1$H-NMR (600 MHz, CDCl$_3$, δ): 7.43 (d, 8H, =CH$_{meta}$; 4-NO$_2$-benzyl); 8.15; 8.18 (2d, 8H, =CH$_{ortho}$; 4-NO$_2$-benzyl) ppm [conformer mixture];

APCI-MS mlz (%): 1040 (MH$^+$, 13)

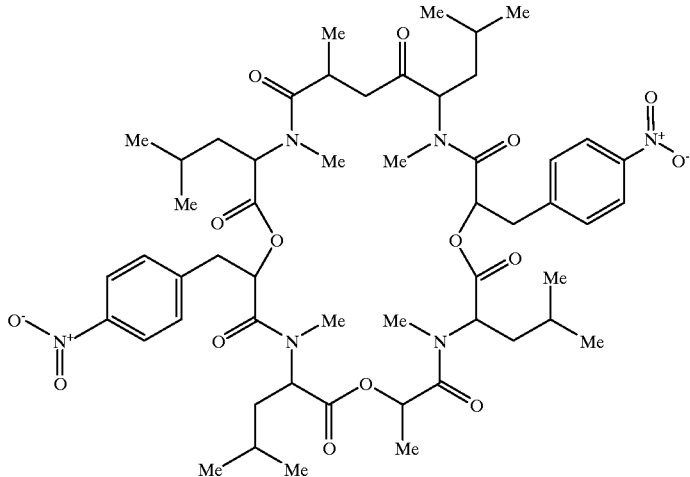

Preparation by Process a
In vivo incorporation of 4-nitro-phenylalanine:

4-Nitro-phenylalanine in a concentration of 50 mM is added under sterile conditions to a main culture of Mycelia sterilia of the species Agonomycetales which is 3 days old and the fermentation is continued for a further 3 days. The mycelium is then removed from the Fusaria culture and, after freeze drying, extracted several times with methanol. The collected organic phases are then evaporated to dryness.

Preparation by Process b
In vivo incorporation of 4-nitro-phenyllactic acid:

4-Nitro-phenyllactic acid in a concentration of 50 mM is added in sterile form to a main culture of Mycelia sterilia of the species Agonomycetales which is 3 days old and the fermentation is continued for a further 3 days. The mycelium is then removed from the Fusaria culture and, after freeze drying, extracted several times with methanol. The collected organic phases are then evaporated to dryness.

In vitm incorporation of 4-nitm-phenyllactic acid:

50–100 μg of enzyme are incubated at 26° C. for two hours in 200 μl of a mixture of 4 mM dithiothreitol, 20% glycerol and tris buffer pH 7.8 with the following substrates:

5 mM ATP,
10 mM MgCl$_2$,
2 mM L-leucine,
0.5 mM S-adenosyl-L-methionine,
2 mM D-lactic acid,
50–100 μM D-4-nitro-phenyllactic acid.

The entire reaction mixture is then extracted with ethyl acetate and the products formed are chromatographed (TLC, HPLC).

The compounds of the general formula (I) shown in Table 1 below can be prepared analogously as LDLDLDLD stereoisomers:

TABLE 1

Examples of compounds of the general formula (I)

(I)

| Ex. No. | R¹ | R² | R³ | R⁴ | Physical Data |
|---|---|---|---|---|---|
| 2 | 4-NO$_2$ | —CH$_3$ | —benzyl | —CH$_3$ | 1017 (M+Na$^+$, 3); 1012 (M+H$_2$O, 18); 995 (MH$^+$, 8)$^{a)}$; 7.37; 7.43 (2d, 4H, =CH$_{meta}$; 4-NO$_2$—benzyl); 8.10 (d, 4H, =CH$_{ortho}$; 4-NO$_2$—benzyl)$^{b)}$ 121.5; 123.6 (4xC$_{ortho}$; 4-NO$_2$—benzyl); 129.3; 130.0 (4xC$_{meta}$; 4-NO$_2$—benzyl)$^{c)}$ |
| 3 | 4-NH$_2$ | CH$_3$ | —benzyl | —CH$_3$ | 986 (M+Na$^+$, 20); 964 (MH$^+$, 100)$^{a)}$; 6.60 (d, 2H, =CH$_{ortho}$; 4-NH-$_2$—benzyl)$^{b)}$ |

$^{a)}$APCI-MS or EI-MS m/z (%)
$^{b)}$¹H-NMR (600 MHz, CDCl$_3$) δ in ppm
$^{c)}$HMQC signals (600 MHz, CDCl$_3$) δ in ppm Cultivation, precultumes and main cultures 1. Cultivation on aear For cultivation of the fungal culture on agar, the following medium is used:

Glucose 2.0%,

Peptone 1.0%,

Yeast extract 1.0%,

Malt extract 1.0%,

KH$_2$PO$_4$ 0.05%,

Arar 1.5%.

Sterilization at 121° C. is then carried out for 20 minutes. The pH of the medium after sterilization is ≈7.0.

2. Liquid culture a) Comsteep/molasses medium:

The Mycelia sterilia strain concerned is cultivated in a medium consisting of molasses (30 g/l), cornsteep liquor (10 g/l) and glucose (30 g/l).

For preparation of a preculture, the medium is inoculated with mycelium from an agar plate and, after about 3 days on a shaking apparatus, used for inoculating further flasks (contents 100 ml each) with the same medium.

b) Alternative medium:

Alternatively, the following medium can also be employed for the cultivation of the fungal culture:

Wheatgerm extract 2.0%,

Pharmamedia 1.0%,

MgSO$_4$.7H$_2$0 0.2%,

NaCl 0.2%,

Starch 2.6%,

Malt syrup 6.0%,

CaCO$_3$ 0.3%.

Sterilization at 121° C. is then carried out for 20 minutes. The pH of the medium after sterilization is 7.5.

For the following feeding experiments, the precursors concerned (e.g. 4-nitrophenylalanine, 4-nitrophenyllactic acid, 4-aminophenylamine, 4-aminophenyllactic acid) are added to 3 day old cultures; the final concentration is 50 mM.

What is claimed is:

1. Process for the preparation of substituted aryllactic acid-containing cyclodepsipeptides having 24 ring atoms of the general formula (I)

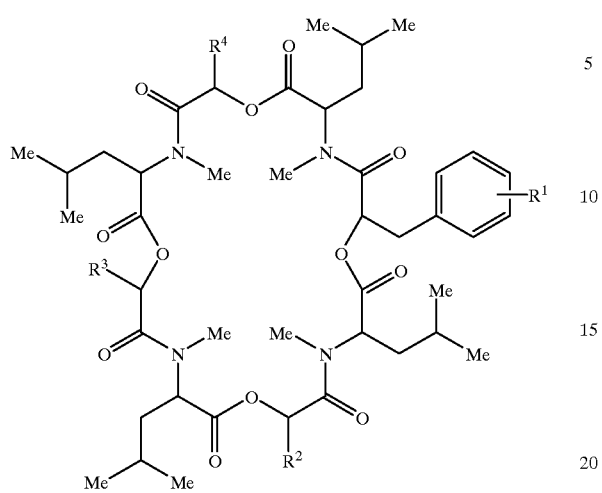
(I)

in which

R¹ represents straight-chain or branched alkyl, cyclic alkyl, alkenyl, alkoxy, alkenyloxy, arylalkoxy, cycloalkoxy, alkylamino, dialkylamino, alkylcarbonyl, alkylcarbonyloxy, alkoxycarbonyl, alkylaminocarbonyl, dialkylaminocarbonyl, heteroarylcarbonyl, alkoxysulfonyl, alkylaminosulfonyl, dialkylaminosulfonyl, alkylthio, alkylsulfinyl, alkylsulfonyl, heteroarylsulfonyl, each of which can optionally be substituted, hydroxyl, halogen, nitro, amino, carboxyl, carbamoyl, cyano, or, if appropriate, substituted cyclic amino groups, and R², R³ and R⁴ independently of one another represent represents straight-chain or branched alkyl, heteroarylmethyl or a benzyl radical which is optionally substituted by radicals from the series consisting of hydrogen, straight-chain or branched alkyl, cyclic alkyl, alkenyl, alkoxy, alkenyloxy, arylalkoxy, cycloalkoxy, alkylamino, dialkylamino, alkylcarbonyl, alkylcarbonyloxy, alkoxycarbonyl, alkylaminocarbonyl, dialkylaminocarbonyl, heteroarylcarbonyl, alkoxysulfonyl, alkylaminosulfonyl, dialkylaminosulfonyl, alkylthio, alkylsulfinyl, alkylsulfonyl, heteroarylsulfonyl, each of which can optionally be substituted, hydroxyl, halogen, nitro, amino, carboxyl, carbamoyl, cyano, or which is optionally substituted by a suitable cyclic amino group, with the exception of the compounds of the formula (I), in which R¹ represents 4-hydroxyl,
R³ represents unsubstituted benzyl and the other radicals have the abovementioned meaning, characterized in that a) optically active or racemic amino acids of the general formulae (II), (III), (IV) and (V)

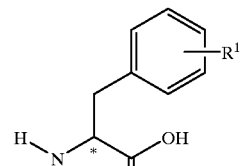
(II)

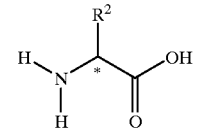
(III)

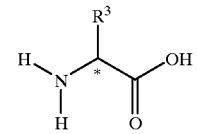
(IV)

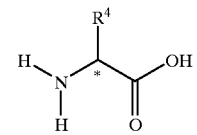
(V)

in which
R¹, R², R³ and R⁴ have the meaning given above, or
b) optically active or racemic 2-hydroxy-carboxylic acids of the general formulae (VI), (VII), (VIII) and (IX)

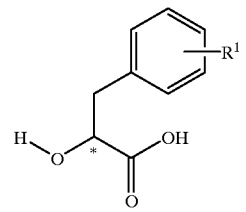
(VI)

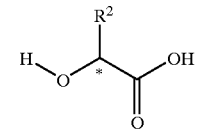
(VII)

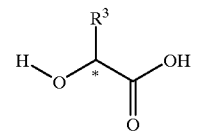
(VIII)

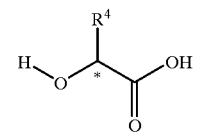
(IX)

in which $R^1$, $R^2$, $R^3$ and $R^4$ have the meaning given above, are reacted in a buffer system in the presence of fungal strains of the species Agonomycetales in suitable nutrient solutions or in the presence of synthetases isolated from these fungal strains and the desired, substituted aryllactic acid-containing cyclodepsipeptides having 24 ring atoms are then isolated.

* * * * *